(12) United States Patent
White

(10) Patent No.: US 6,254,383 B1
(45) Date of Patent: Jul. 3, 2001

(54) SYSTEM FOR HANDLING DENTAL ELASTICS

(75) Inventor: Velton C. White, West 590 Kearney Rd., Burlington, WI (US) 53105

(73) Assignee: Velton C. White, Burlington, WI (US)

( * ) Notice: Subject to any disclaimer, the term of this patent is extended or adjusted under 35 U.S.C. 154(b) by 0 days.

(21) Appl. No.: 09/310,019

(22) Filed: May 11, 1999

Related U.S. Application Data

(60) Provisional application No. 60/085,686, filed on May 15, 1998.

(51) Int. Cl.[7] ............................................. A61C 3/00
(52) U.S. Cl. ................................. 433/18; 433/3; 206/820
(58) Field of Search ........................ 433/3 R, 11, 18 OR; 206/820 R

(56) References Cited

U.S. PATENT DOCUMENTS

| | | | |
|---|---|---|---|
| 4,001,940 | 1/1977 | Cusato | 433/3 |
| 4,038,753 | 8/1977 | Klein | 433/18 |
| 4,260,374 | 4/1981 | Kurz | 433/3 |
| 4,277,236 | 7/1981 | Kurz | 433/3 |
| 4,412,820 * | 11/1983 | Brummond et al. | 433/18 |
| 4,901,847 | 2/1990 | Kesling | 206/63.5 |
| 4,921,423 | 5/1990 | Kesling | 433/3 |
| 4,946,385 * | 8/1990 | Eckert et al. | 433/18 |
| 5,013,238 * | 5/1991 | Sterrett et al. | 433/18 |
| 5,984,674 * | 11/1999 | Klein | 433/18 |

* cited by examiner

*Primary Examiner*—John J. Wilson
(74) *Attorney, Agent, or Firm*—Marsh, Fischmann & Breyfogle LLP

(57) ABSTRACT

An improved dental elastic handling system is disclosed. The system is directed to the use of one or more assemblies which each include a plurality of elastics interconnected to a runner. The system may comprise an inventive dispenser having a tubular member with a channel therethrough for receiving an elastics runner assembly. The tubular member may include a slot extending from one end to a mid-portion. A cutting edge may be provided at the distal end of the slot. Upon positioning an elastics/runner assembly within the channel of the dispenser, the elastics will extend through the slot a predetermined distance to facilitate grasping by a placement device. By opposing advancement of the dispenser and/or elastics/runner assembly the elastics may selectively contact the cutting edge of the dispenser so as to facilitate disengagement of the elastics. The arrangement provides for enhanced carrying, cutting and installation of dental elastics.

29 Claims, 6 Drawing Sheets

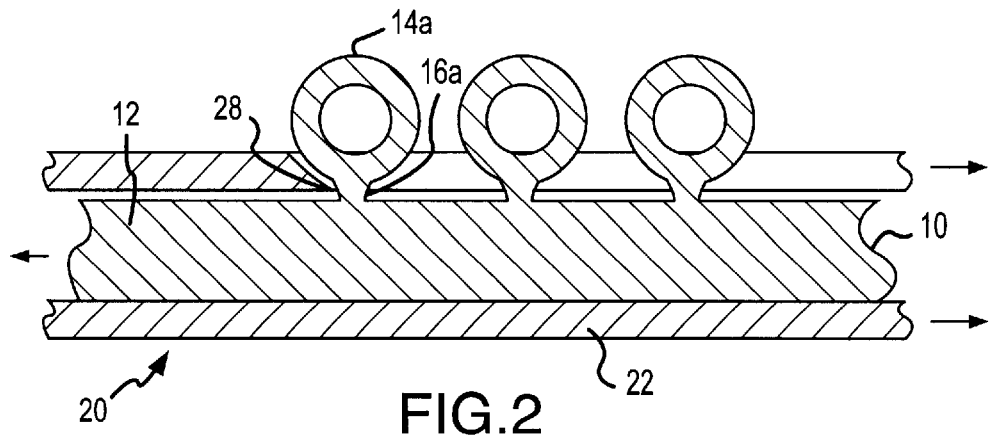
FIG.2
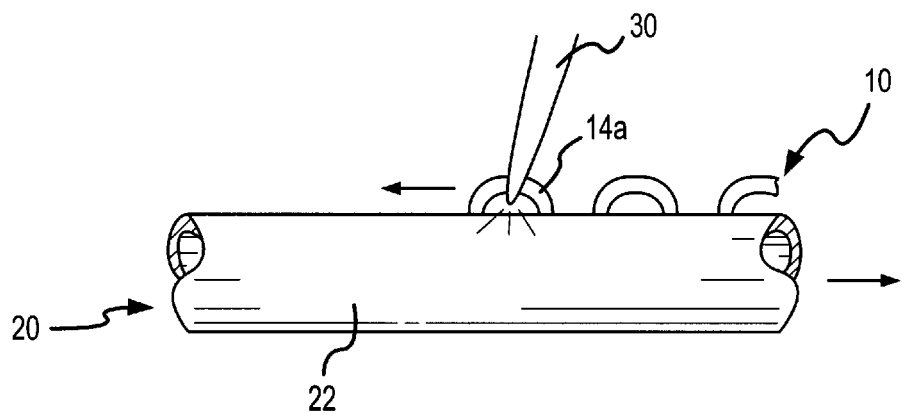
FIG.3A
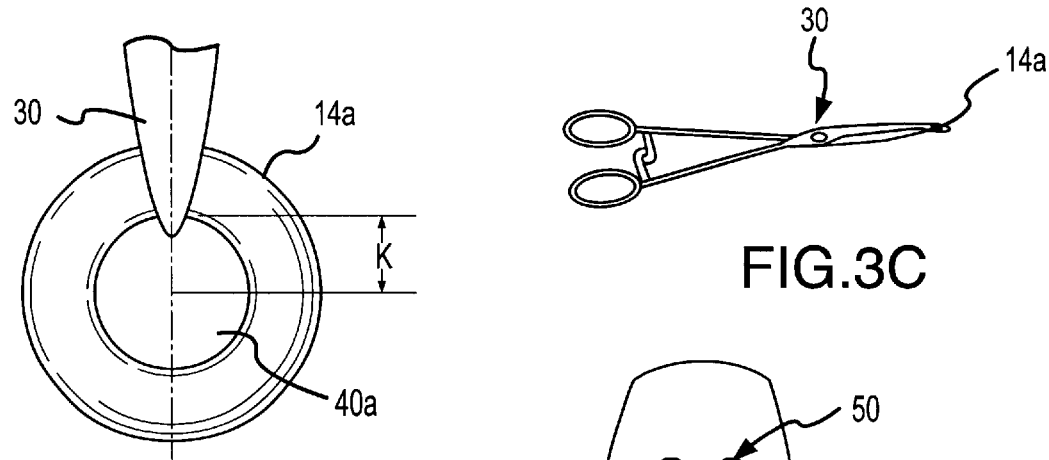
FIG.3B
FIG.3C
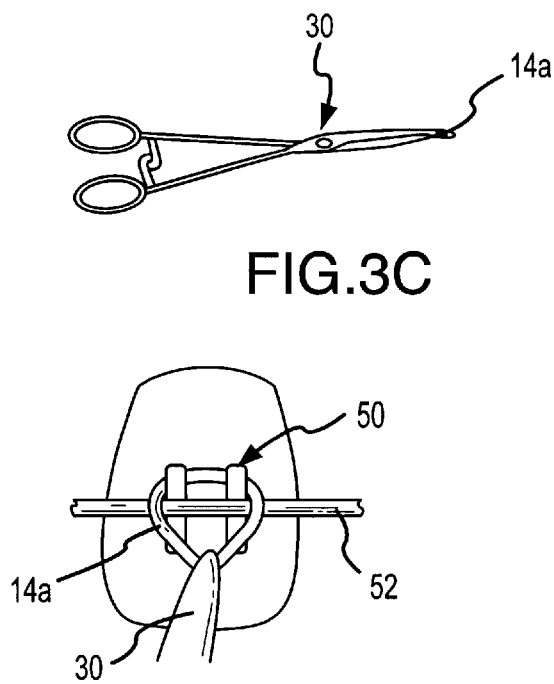
FIG.3D

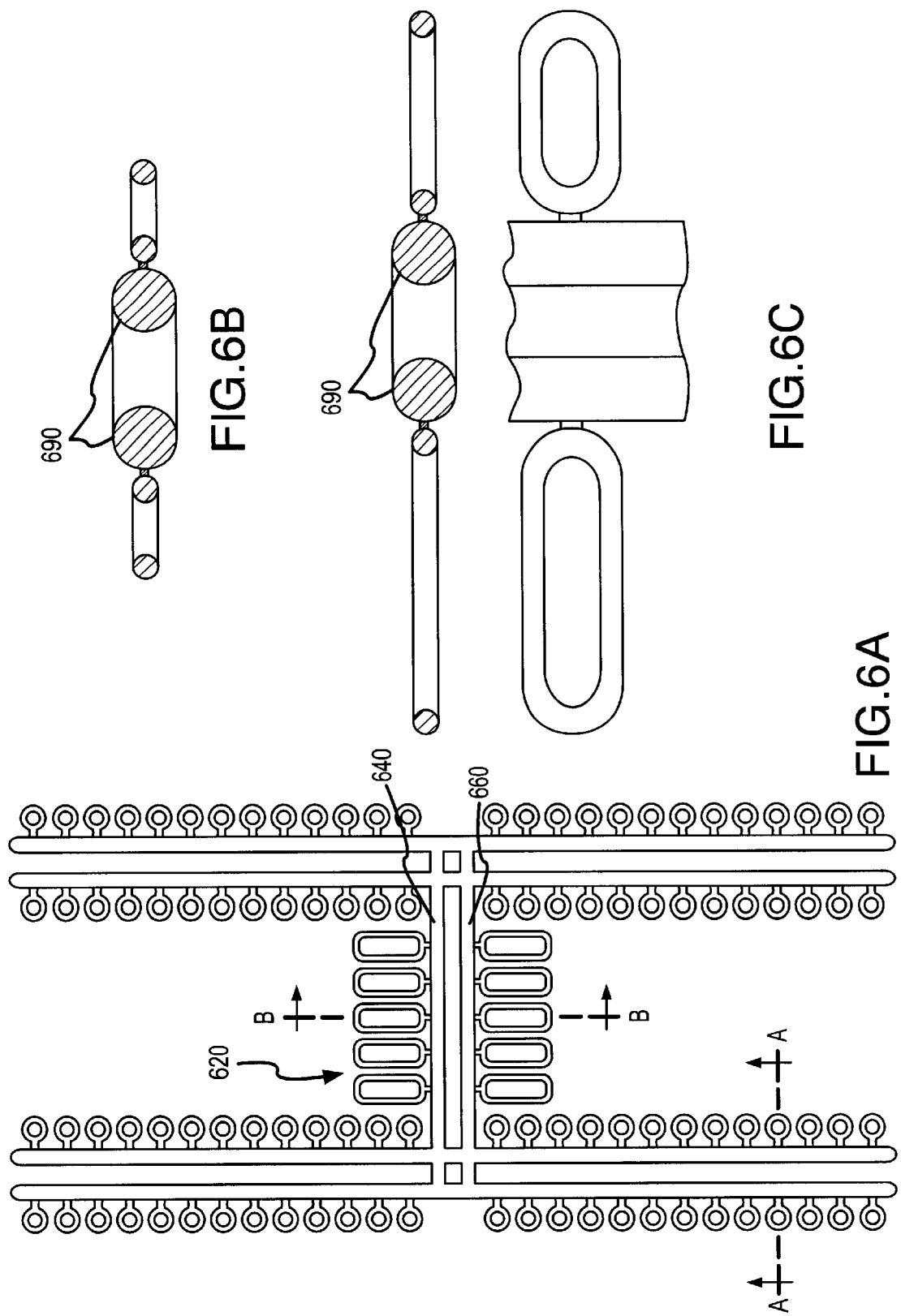

SYSTEM FOR HANDLING DENTAL ELASTICS

RELATED APPLICATION

This application claims the benefit of U.S. Provisional Application Ser. No. 60/085,686 filed on May 15, 1998 entitled "SYSTEM FOR HANDLING DENTAL ELASTICS".

FIELD OF THE INVENTION

The present invention pertains to the handling of dental elastics, and more particularly, to a system for carrying, dispensing, and installing dental elastics.

BACKGROUND OF THE INVENTION

Orthodontic ligatures, dental separating rings and synthetic elastics, collectively referred to herein as "dental elastics," are widely employed to selectively interconnect various orthodontic and dental appliances (e.g., orthodontic brackets, wire, springs and accessories), as may be determined to be appropriate by practitioners on a case-by-case basis. Such elastics are generally toroidally-shaped and fabricated from resilient materials.

While early elastics were individually cut from surgical latex tubing, elastics are now generally molded and integrally interconnected to a "stick" carrier, wherein the number of ligatures on a stick is sufficient to fulfill the requirements for a given patient visit. In this regard, the packaging of elastics has been driven by greater awareness of infection control and sterilization requirements, wherein any elastics on a stick that are not utilized in conjunction with a given patient visit may be disposed of at a relatively low waste expense.

Typically, the disconnection of elastics from a stick carrier is accomplished by grasping an elastic with a placement tool and pulling the elastic away from the stick. As will be appreciated, such a procedure can stretch and thereby damage the elastics (e.g., due to permanent deformation effects), thereby adversely impacting the intended performance. Further, handling of an elastic via manipulation of a placement tool (i.e., to establish proper grasping of the elastic for installation) can be tedious for dental and orthodontic practitioners.

SUMMARY OF THE INVENTION

The primary objective of the present invention is to provide an improved system for carrying, dispensing and/or installing elastics.

More particularly, it is an object of the present invention to provide an improved method and device for disconnecting elastics from a carrier.

A further object is to provide an improved method and device for facilitating selective grasping of an elastic with a placement instrument so as to facilitate installation of the elastic within a patient's mouth.

Yet another objective of the present invention is to provide for the improved carrying, or packaging, of elastics to provide enhanced ease-of-use by practitioners.

One or more of these objectives and additional advantages can be realized by the present invention which is directed to the handling of elastics interconnected to a carrier member or runner. The runner may be sized for hand manipulation by a practitioner and may have a plurality of interconnected via corresponding connectors in an aligned manner along at least one side of the runner. Such elastics will generally have an opening therethrough for selective interconnection with orthodontic componentry (e.g. brackets).

In one aspect of the invention, the invention comprises a separate dispenser for receiving an elastics/runner assembly and for engaging one or more of the corresponding connectors to facilitate the selective disengagement of one or more corresponding elastics from the runner. The dispenser may be of a tubular construction with an internal passageway or channel passing therethrough, such channel being sized to matingly and slidably receive at least a portion of the runner therethrough. Further, the dispenser may include a slot that extends from at least one end of the dispenser and through which elastics/connectors that are interconnected to the carrier may project. Preferably such slot is linearly disposed and is of a width that accommodates the passage of elastics and/or connectors therethrough. An end or side portion of the slot may be provided with a cutting edge to facilitate disconnection of the elastics from the runner. The elastics may be shaped so as to define a circular, oval, square, rectangular or other opening shape therethrough.

In use, one end of the runner may be inserted into the channel of a slotted end of the dispenser with the interconnected elastics projecting outwardly from the dispenser through the slot thereof. The leading elastic may then be grasped by a placement tool (e.g., held by one hand) and the dispenser may be held (e.g., by the other hand). Either or both of the runner and dispenser may then be opposingly advanced until the leading elastic has engaged the cutting edge of the slot (e.g, at a closed end of the slot) and disengaged from the runner. Preferably, disengagement occurs as a combinative result of a pulling and severing action.

In another aspect of the invention, the elastics/runner assembly and dispenser can be correspondingly sized so that only a predetermined portion of each elastic will project through the slot of the dispenser to facilitate ready grasping by a placement instrument and installation in a patient's mouth by a practitioner. In this regard, the elastic should project through the slot so that at least a portion of the elastic opening is located outside of the dispenser. Preferably, the exposed portion of the elastic opening should not exceed about one-half of the opening, and most preferably the exposed portion should comprise about one-quarter of the opening. Such positioning facilitates easy and effective grasping of the elastic by the placement device and facilitates subsequent installation of the elastic in a patient's mouth. That is, for example, by limiting the grasping of an elastic to about one-half, or most preferably one-quarter, of its opening, the elastic opening in the ungrasped portion is still accessible for ready placement over or around an orthodontic or dental appliance during installation.

In a related aspect of the present invention, the width of the dispenser slot should preferably be less than the width of the nose or beak of the placement tool utilized to grasp, disconnect and install an elastic. Such relative sizing facilitates the above-noted grasping and installation functions by providing a "positive stop" arrangement.

In an additional aspect of the present invention, at least a portion of the slot in the dispenser and an interfacing portion of an elastics/runner assembly may be configured to provide for a slight interference therebetween, wherein the elastics/runner assembly will be lightly restrained from independently sliding out of the dispenser channel after insertion thereinto. Of course, such interface should not prevent advancement of the elastics/runner assembly through the channel or removal therefrom when desired. The noted restraining interface may be provided by reducing the slot width at the open end thereof so as to be slightly less than the width of the resilient elastics and/or resilient connectors extending therethrough. Alternatively, an internal surface of the channel of the dispenser and/or a portion of the runner may be sized so as to provide the noted interference. Further, a retaining interference may be obtained from the frictional engagement of the severed connectors inside the dispenser in order to prevent the runner from independently sliding out of the dispenser after all of the dental elastics have been removed from the runner. Numerous additional techniques for achieving the noted retentive effect are also possible.

In yet another aspect of the present invention, a plurality of elastics/runner assemblies may be interconnected and packaged as a unit. By way of example, such plurality of assemblies may be interconnected in an H-shaped configuration. Further, the elastics interconnected to at least one of the plurality of assemblies may be differently sized and/or shaped from the elastics interconnected to the other assemblies. In the later regard, the elastics connected to certain assemblies may be toroidal while the elastics connected to one or more other assemblies may be of a round, rectangular or square configuration. Additionally, one or more of the assemblies may be provided with elastics extending along only one side thereof, while one or more of the assemblies may be provided with elastics extending off of two or more sides thereof. Each of the assemblies may be selectively disconnected from the balance at reduced sections adjoining adjacent runners and readily utilized with a dispenser as noted above.

In a further aspect of the present invention, the above-noted dispenser may be provided with a separate extension for facilitating handling of the same. In one arrangement, a ring may be interconnected to the dispenser for positioning about the finger of the practitioner. In another arrangement, the extension could merely comprise a tab for grasping between the fingers of a practitioner.

In yet another aspect of the present invention, two or more dispensers may be interconnected for separate receipt of two or more runner carrier/elastic assemblies therethrough. Such an arrangement facilitates ready dispensation of the elastics where two or more colors or sizes are provided by separate assemblies. In such an arrangement, a single extension may be utilized for handling of the interconnected dispensers. Such extension may take the form of a simple adjoining flange having a width sufficient to accommodate the thumb and forefinger of a practitioner. Alternatively, a single ring-shaped extension may be interconnected to one or more of the interconnected dispensers for ready positioning on the finger of a practitioner.

Numerous additional embodiments of the present invention are possible. For instance, a plurality of dispensers may be interconnected so that a corresponding plurality of different colors of dental elastic/runner assemblies are readily available for installation according to a patient's color preference. In addition, dispensers may be constructed of a transparent material so that the color of a dental elastic/runner assembly can be readily observed. Alternatively, the dispenser may be of a color to match the color of the elastics dispensed thereby. Moreover, the dispenser of the present invention may include a mounting arrangement so that it can be mounted to the wall or other stationary fixtures, such as an operatory furniture structure. Further, the dispenser may have a tongue and a complementary groove (or dovetail features) formed along the outer surface of the tubular member to permit multiple dispensers to slide together and lock as a single dispensing unit. Furthermore, a display rack may be provided to releasably support a plurality of dispensers, each dispenser containing elastics of a different color. In this way, patients are able to select the colors they want. The dispensers chosen by the patient can be taken from the display rack and engaged to each other via the tongue and groove (or dovetail) features. The connected dispensers may then be clipped onto a ring for finger dispensing. Alternatively, the connected dispensers may be fitted onto a clip rigidly mounted to a operatory equipment to permit one-handed dispensing.

Numerous extensions and additional advantages will become apparent upon further consideration of the embodiments which follow.

DESCRIPTION OF THE DRAWINGS

FIG. 2 is a front cross-sectional view of the elastics/runner assembly of FIG. 1A positioned within the dispenser of FIG. 1B.

FIG. 3A is a partial front view of the nose of a placement device grasping an elastic projecting from a dispenser in one embodiment of the present invention.

FIG. 3B is a partial enlarged view of the nose of a placement device grasping a disconnected elastic.

FIG. 3C is a plan view of a placement device having an elastic grasped thereby.

FIG. 3D is a front view of a disconnected elastic being positioned on an orthodontic bracket via manipulation of the nose of a placement device.

FIG. 6A illustrates another embodiment of an H-configuration of a plurality of interconnected elastic/runner assemblies.

FIG. 6B is a cross-sectional elevational view of the elastic/runner assemblies taken along the line A—A of FIG. 6A.

FIG. 6C is a cross-sectional elevational view of the elastic/runner assemblies taken along the line B—B of FIG. 6A and a top plan view of corresponding dental elastics extending from the runners.

DETAILED DESCRIPTION

Figure 1A:
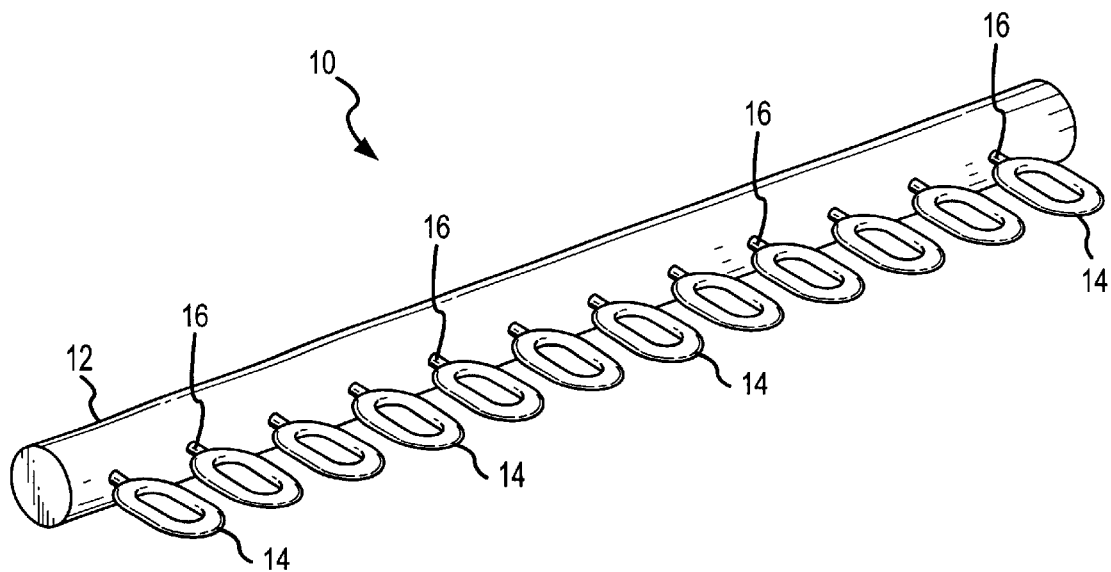
FIG. 1A is a perspective view of an elastics/runner assembly comprising one embodiment of the present invention.

FIG. 1A illustrates an elastics/runner assembly 10 that includes an elongated runner 12 and a plurality of ring-shaped elastic members 14 extending from one side of runner 12 in an aligned fashion. Each of the elastics 14 are interconnected by a corresponding connector 16 to the runner 12. As will be appreciated, the assembly 10 may be integrally molded from any of a plurality of elastomeric materials (e.g., a urethane or other synthetic material).

Figure 1B:
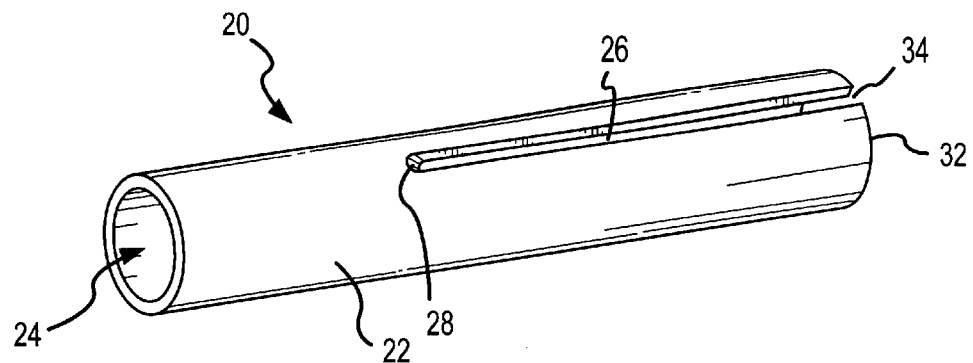
FIG. 1B is a perspective view of a dispenser comprising one embodiment of the present invention.

FIG. 1B illustrates a dispenser 20 for use in handling an elastics/runner assembly, such as assembly 10 and disconnecting the elastics 14 from runner 12. More particularly, the dispenser 20 includes an elongated, tubular member 22 having an opening 24 extending therethrough. Dispenser 20 further includes a slot 26 extending from one end 32 of the tubular member 22. A cutting edge 28 is provided at the closed end of slot 26. One or more of the longitudinally extending side edges of slot 26 may also comprise a cutting edge. Dispenser 20 may be fabricated from a metal (e.g., aluminum or stainless steel), or a plastic (e.g., polystyrenes or polycarbonates). Other plastics such as polyesters or polyethersulfones may also be employed to facilitate sterilization for re-use after a given patient visit. Fabrication from a plastic material is particularly apt for disposable implementations. It should be noted that both cold sterilization (e.g. gluteraldehyde) and heat sterilization methods (e.g. including dry heat sterilization) and autoclave sterilization are possible with the dispensers molded from the plastics mentioned above. In one embodiment, the dispenser may be molded from a transparent material so that the color of dental elastic/runner assembly can be readily observed.

The cross-sectional configuration and size of the runner 12 can be established in relation to the cross-sectional configuration and size of opening 24 through tubular member 22 such that the runner 12 may be conformly and slidably received within opening 24 at the first end 32 of tubular member 22. While not shown, the open end 34 of slot 26 may be slightly reduced in width to provide for a slight interference with the resilient elastics 14 and/or connectors 16, thereby serving to slightly retain assembly 10 in dispenser 20. Further in this regard, and as best illustrated in FIG. 2, the relative dimensions of the elastics/runner assembly 10 and dispenser 20 can be advantageously established so that the elastics 14 will extend through the slot 26a of predetermined amount for ready grasping by a placement device, as will be further described.

With further reference to FIG. 2, the cutting edge 28 at the distal end of the slot 26 is shown near engagement with a connector 16a of one of the elastics 14a. As will be appreciated, opposing advancement of either the dispenser 20 or assembly 10 will cause cutting edge 28 to engage connector 16a. Such engagement together with the noted opposing advancement serve to disconnect elastic 14a from the runner 12.

In this regard, and as illustrated in FIG. 3A such advancement may occur while a hand manipulated placement device 30 has engaged the elastic 14a. In this regard, the nose of the placement device 30 should preferably engage the elastic 14a so that the tip of the nose does not extend more than half way across the opening 40a through the elastic 14a (i.e., the nose should be within the range designated as "k" in FIG. 3B), and most preferably the nose should be located about one-quarter across opening 40a. As will be appreciated, the above-noted relative sizing of the elastics/runner assembly 10 and dispenser 20 serves to provide an arrangement whereby the elastics 14 project outward from the slot 26 of the dispenser 20 a predetermined amount so as to facilitate the noted, desired engagement or grasping of elastics 14 by the nose of a placement device 30. Further in this regard, the width of slot 26 is established so that elastics 14 and connectors 16 will slidably pass therethrough during use, but so that the nose of the placement device 30 will not project therethrough and instead will contact the outer surface of the tubular member 22 to ensure the desired grasping of elastics 14 for installation.

Further in this regard, FIG. 3C illustrates an exemplary placement device 30 having an elastic 14a grasped thereby in accordance with the present invention. The placement device 30 illustrated in FIG. 3C is of a hemostat-type configuration. As will be appreciated by those skilled in the art, a variety of other placement devices may be utilized in conjunction with the present invention. In any case, by accommodating the grasping of an elastic 14 within a predetermined position range "k" on an elastic 14, a system is provided that facilitates ready placement of the grasped elastic 14 in a patient's mouth.

More particularly, and as shown by way of example in FIG. 3D, the opening 40a of an elastic 14a may be readily positioned on the gingival tie wings of a bracket 50 positioned on a tooth in the upper arch of a patient's mouth, wherein the elastic 14a may then be elastically pulled over the occlusal tie wings of the bracket 50 to secure an arch wire 52 within the slot of the bracket 50. Numerous additional applications will be apparent to those skilled in the art.

Figure 4A:
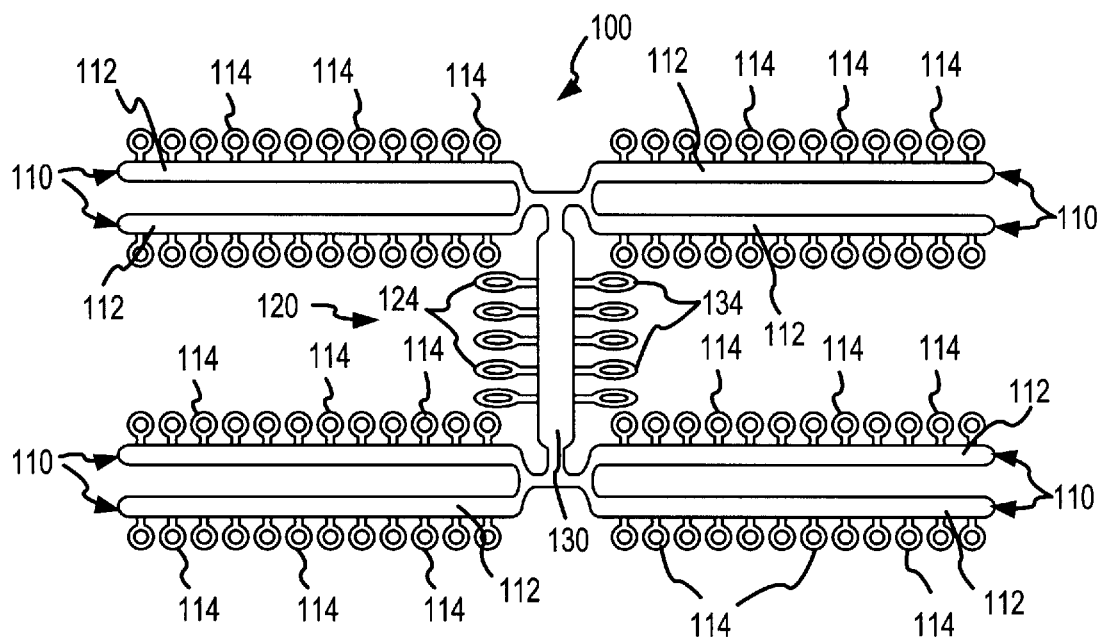
FIG. 4A illustrates an H-configuration of a plurality of interconnected elastics/carrier assemblies comprising an embodiment of the present invention.

FIG. 4A illustrates an embodiment 100 having a plurality of commonly-configured elastics/runner assemblies 110 interconnected via a cross-member elastics/runner assembly 120. More particularly, four pairs of elastics/runner assemblies 110 and a single cross-member elastics/runner assembly 120 may be interconnected in an H-shaped configuration, wherein the assemblies 110 are each oriented so that their corresponding interconnected elastics 114 project outwardly from the corresponding runners 112. Further, the cross-member assembly 120 may be provided with elastics 124, 134 extending outward from the carrier 130 on two opposing sides thereof. The elastics 124, 134 may be conveniently sized differently for different applications than the elastics 114 extending from the assemblies 110. By way of example, the elastics 114 of assemblies 110 may have a 3 millimeter inside opening diameter while the elastics 124 and 134 may have an inside opening diameter of 9 millimeters and 6 millimeters, respectively. Further in this regard, the elastics 124 and 134 may be provided in shapes other than a round or toroidal shape as is customary. By way of example, the elastics 124, 134 may be generally square or rectangular in shape as per FIG. 4C. As will be appreciated, the rectangular shape of elastics 124, 134 illustrated in FIG. 4C may more closely reflect the configuration to be resiliently assumed upon installation of elastics 124, 134, thereby yielding enhanced performance (e.g., extended wear). In one arrangement elastics 124 may have a 3 mm×9 mm rectangular opening while elastics 134 may have a 3 mm×6 mm rectangular opening. It is also noted that the various assemblies 110, 120 may be provided in differing colors (e.g., via a selectively gated molding production process).

In one embodiment and as shown in FIG. 6A, the horizontal cross member 620 comprises a pair of elastics/runner assemblies 640 and 660. Each assembly has elastics projecting from one side of the runner. The runners 680 of the cross member are substantially similar in diameter to each of the four pairs of runners 690 as shown in FIGS. 6B and 6C.

More generally, and as will be appreciated, the embodiment 100 may be integrally molded and conveniently packaged as a single unit. In use, each of the assemblies 110 may be readily disconnected at the reduced cross-sectional adjoining regions 140 and then utilized with a dispenser, such as that shown in FIG. 1B in the manner described hereinabove.

Figure 4B:
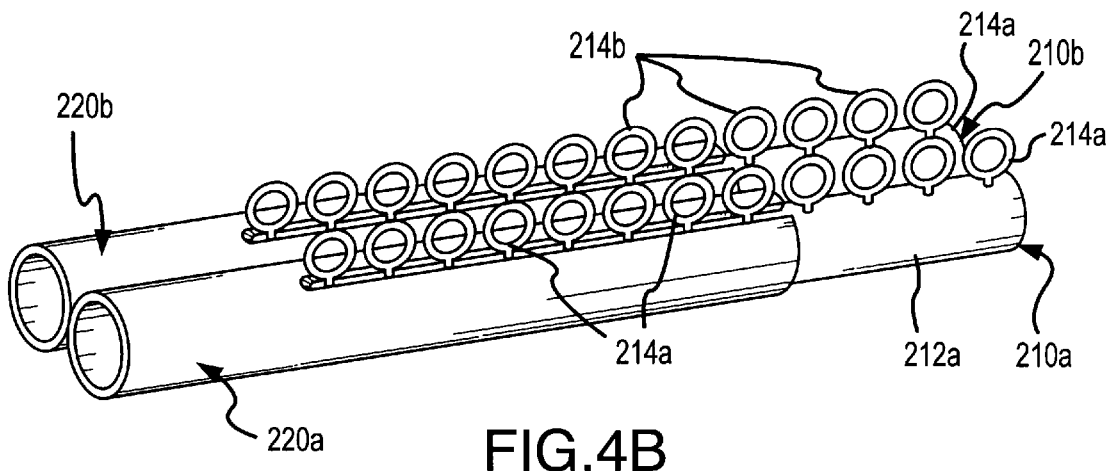
FIG. 4B illustrates two interconnected dispensers having separate elastic/runner carrier assemblies positioned therewithin.
Figure 4C:
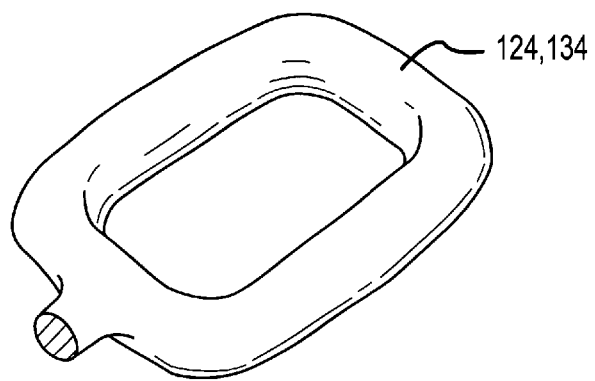
FIG. 4C illustrates an alternative configuration for a dental elastic in one embodiment of the present invention.

FIG. 4B illustrates two interconnected dispensers 220a and 220b. By way of example, if dispensers 120a, 120b are metal, interconnection may be established via brazing or soldering; if the dispensers 120a, 120b are plastic, interconnection may be via molding. It should be noted that the metal dispensers may also be casted unitarily such as with a cast aluminum version. Each of the dispensers 220a and 220b are illustrated with separate elastics/runner assemblies 210a, 210b positioned therewithin. Such an arrangement may be conveniently utilized when two different colors of elastics 214a, 214b may be desired by a patient (e.g., for purposes of displaying school colors, seasonal/holiday colors, or other personal expressions). That is, the elastics 214a on runner 212a may be one color while the elastics 214b on the runner 212b may be another color. The provision of a single interconnected dispenser structure for handling each of the two colors of elastics provides manipulation and other handling advantages to a practitioner.

Figure 5A:
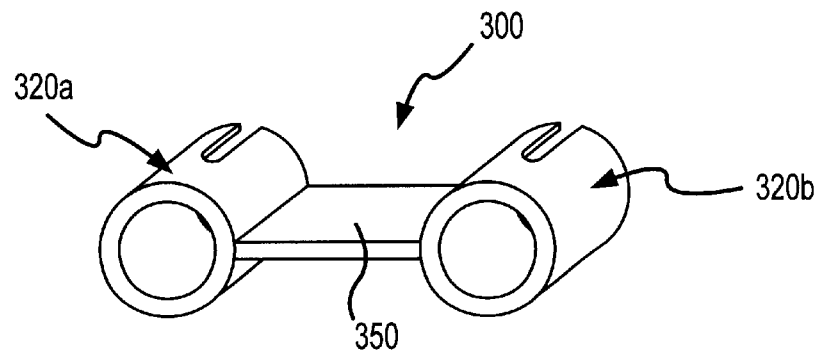
FIG. 5A illustrates two slotted dispensers interconnected by a central flange adapted for finger-held manipulation.
Figure 7:
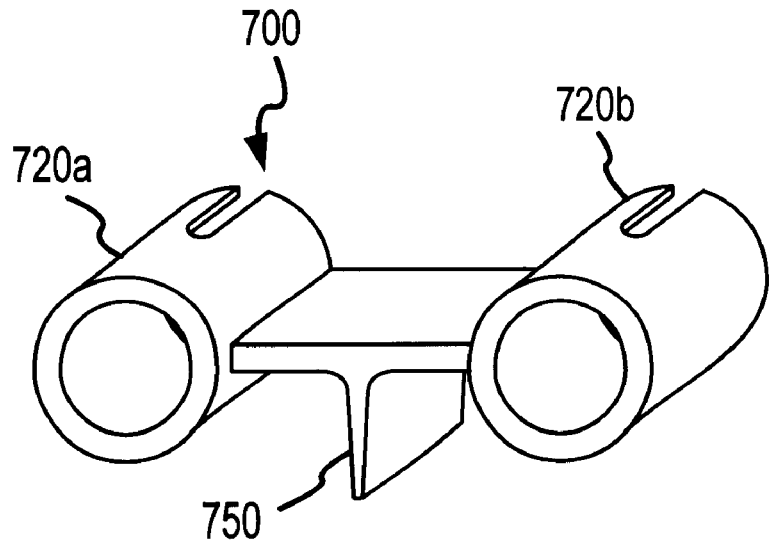
FIG. 7 illustrates another embodiment of two dispensers interconnected by a T-shaped flange.

Further in this regard, FIG. 5A illustrates a dual dispenser 300 having two dispensers 320a and 320b interconnected via a flange member 350. The flange member 350 may be sized for grasping between the thumb and index finger of a practitioner. The flange member may take any other suitable shape as would be appreciated by those skilled in the art. For example, FIG. 7 illustrates another embodiment of a dual dispenser 700 having two dispensers 720a and 720b interconnected via a T-shaped flange member 750.

Figure 5B:
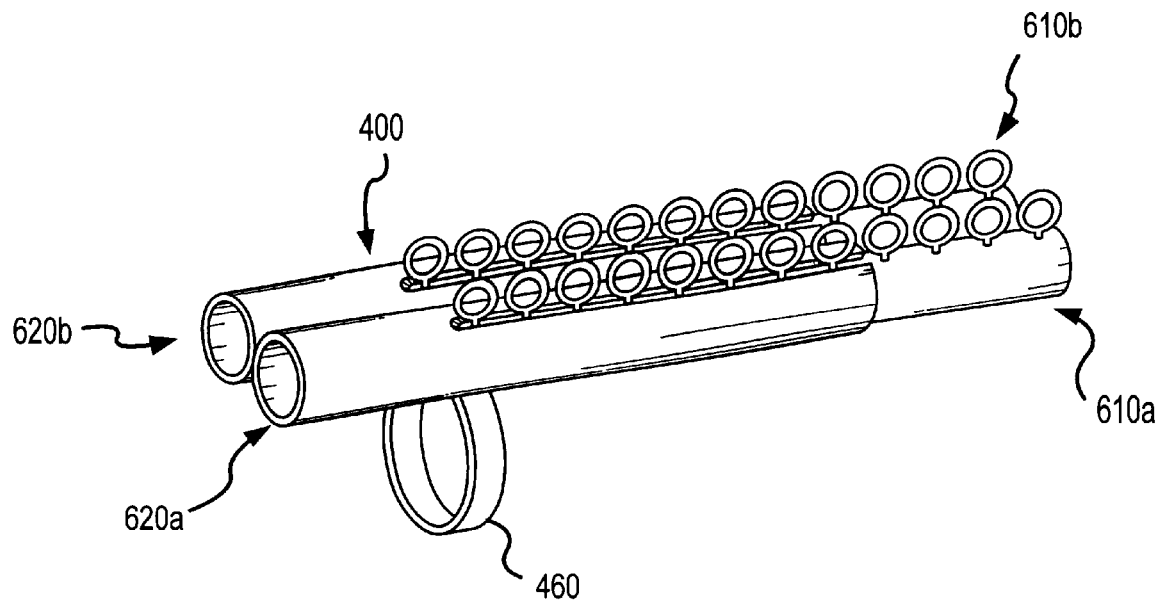
FIG. 5B illustrates two interconnected dispensers having a ring-shaped extension interconnected therewith.

FIG. 5B illustrates another dispenser arrangement 400. More particularly, a ring-shape extension 460 is interconnected to interconnected dispensers 420a and 420b and may be readily positioned on a finger of a practitioner during use. Such an arrangement facilitates chair-side procedures by conserving real-estate and by allowing a practitioner to handle other equipment while still conveniently holding the elastics/runner assemblies 610a, 610b near the patient. That is, the dispenser 400 may be placed on a finger of the left hand of a practitioner while the right hand manipulates a placement tool. Obviously, the ring-shaped extension 460 shown in FIG. 5B may also be utilized with a single dispenser arrangement.

Figure 8:
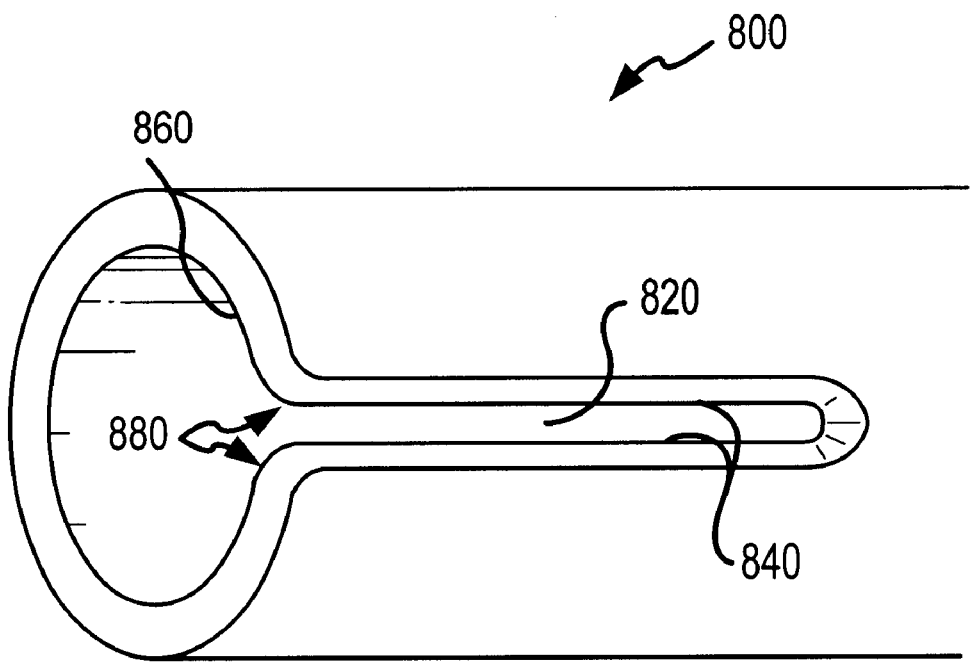
FIG. 8 is a perspective view of a slot of a dispenser comprising one embodiment of the present invention.

In one embodiment and as shown in FIG. 8, the open end 860 of the slot 820 has a funnel configuration to help facilitate loading of the dispenser 800 with the dental elastic/runner assembly. The slot 820 includes two side walls 840 terminating in a tapered opening 880 of a predetermined width. The tapered opening 880 is sized to aid in slidably receiving of the elastic members and corresponding connectors into the slot.

Numerous additional embodiments will be apparent to those skilled in the art and are intended to be within the scope of the present invention.

What is claimed is:

1. A dispenser for use in handling a dental elastic/runner assembly having a runner and a plurality of dental elastic members extending from the runner via corresponding connectors, comprising:
   a tubular member having an opening extending therethrough for slidably receiving and removing, at an open end thereof, at least a portion of a runner of a dental elastic/runner assembly; and,
   a slot, extending outward from said opening through and along the tubing member from said open end of the tubular member, for accommodating the passage of a plurality of dental, ring-shaped elastic members and corresponding connectors of a dental elastic/runner assembly, wherein said slot includes at least one of (i) a closed end with a cutting edge for engaging a leading connector of a dental elastic/runner assembly to facilitate disengagement of a corresponding elastic member, and (ii) a side portion having a cutting edge for engaging at least one or more connectors of a dental elastic/runner assembly to facilitate disengagement of at least one or more corresponding elastic members.

2. The dispenser as claimed in claim 1, wherein at least one of the tubular member and the slot is sized to provide a retaining interference between the dispenser and a dental elastic/runner assembly.

3. The dispenser as claimed in claim 1, wherein an interior cross-sectional configuration and size of said opening of said tubular member is selected in relation to an exterior cross-sectional configuration and size of a runner of a dental elastic/runner assembly such that the runner is matingly and slidably received within said opening of said tubular member.

4. The dispenser as claimed in claim 1, wherein said slot is linearly disposed.

5. The dispenser as claimed in claim 1, comprising at least two tubular members interconnected in a parallel relationship.

6. The dispenser of claim 5, further comprising a ring-shaped extension interconnected to said at least two interconnected tubular members so as to allow a practitioner to position the dispenser on his/her finger during use.

7. The dispenser as claimed in claim 1, comprising two tubular members interconnected via a flange member, wherein said flange member is sized for grasping between the thumb and index finger of a practitioner.

8. The dispenser as claims in claim 1, wherein:
   said tubular member is sized so that at least a portion of an opening of a dental elastic member of a dental elastic/runner assembly is located outside of the dispenser when a runner of the elastic runner assembly is received within said opening thereby facilitating ready grasping by a placement tool.

9. The dispenser as claimed in claim 8 wherein said portion of the elastic opening located outside of the dispenser is less than about one-half of said elastic opening.

10. The dispenser as claimed in claim 9, wherein said portion of the elastic opening located outside of the dispenser is about one-quarter of said elastic opening.

11. A dental elastic/runner assembly, comprising:
   a pair of dental elastic/runner subassemblies connected together to form a single integral unit;
   each dental elastic/runner subassembly of said pair including an elongated runner, a plurality of dental elastic members, and a plurality of connectors, each of said connectors being interconnected between said elongated runner and one of said elastic members; and
   wherein one of said dental elastic/runner subassemblies has the dental elastic members extending toward one side of the assembly and the other of said dental elastic/runner subassemblies has the dental elastic members extending toward the other side of said assembly and wherein said dental elastic/runner subassemblies are connected together at a reduced cross-sectional adjoining region.

12. The dental elastic/runner assembly as claimed in claim 11, wherein said dental elastic/runner subassemblies comprising said par are aligned in a side-by-side, substantially parallel relationship and connected to each other at least at one end thereof.

13. The dental elastic/runner assembly as claimed in claim 11, comprising a first pair of dental elastic subassemblies interconnected to a second pair of dental elastic subassemblies so as to extend along the same longitudinal axis.

14. The dental elastic/runner assembly as claimed in claim 13, further comprising four pairs of dental elastic/runner subassemblies and a single cross-member elastic/runner subassembly interconnected in an H-shaped configuration.

15. The dental elastic/runner assembly as claimed in claim 14, wherein said elastic members attached to said four pairs of dental elastic/runner subassemblies are of a different size than the size of said elastic members attached to said cross-member elastic/runner subassembly.

16. The dental elastic/runner assembly as claimed in claim 11, wherein said elastic members attached to at least one of said elastic/runner subassemblies are of a different shape than the shape of said elastic members attached to other elastic/runner subassemblies.

17. The dental elastic/runner assembly as claimed in claim 11, wherein at least a portion of said elastic members is generally of a round shape and at least a portion of said elastic members is generally of a rectangular shape.

18. The dental elastic/runner assembly as claimed in claim 11, wherein said elastic members attached to at least one of said elastic/runner subassemblies are generally of different color than the color of said elastic members attached to other elastic/runner subassemblies.

19. A system for handling dental elastic members, comprising:

an elastic/runner assembly including an elongated runner, a plurality of ring-shaped dental elastic members, and a plurality of connectors, each of said connectors interconnected between said elongated runner and one of said elastic members; and, a dispenser including a tubular member having (i) an opening extending therethrough that slidably and removably receives, at an open end thereof, at least a portion of said runner therethrough, and (ii) a slot extending outward from said opening through the tubing member from said open end, wherein said dispenser is sized such that at least a portion of said dental elastic members is located outside of the dispenser when said dental elastic members project through the dispenser slot.

20. A system for handling dental elastic members as claimed in claim 19, further comprising a hand manipulated placement tool having a nose for engaging one of said elastic member, wherein the width of said nose is greater than the width of said dispenser slot such that outer surfaces of the tubular member adjacent to the slot serve as a positive stop arrangement for the placement tool.

21. The system for handling dental elastic members as claimed in claim 20, wherein:

each of said elastic members has an elastic opening; and said elastics/runner assembly and said dispenser are correspondingly sized such that at least a portion of said elastic opening is located outside of the dispenser when said elastic members project through the dispenser slot in order to facilitate ready grasping by said placement tool.

22. The system for handling dental elastic members as claimed in claim 21, wherein said portion of the elastic opening located outside of the dispenser is less than about one-half of said elastic opening.

23. The system for handling dental elastic members as claimed in claim 22, wherein said portion of the elastic opening located outside of the dispenser is about one-quarter of said elastic opening.

24. The system for handling dental elastic members as claimed in claim 19, wherein at least one of the runner, the dental elastic members, and the connectors is sized to provide a slight interference between the dispenser and the dental elastic/runner assembly, whereby said elastic/runner assembly is lightly restrained from independently sliding out of said dispenser opening after insertion thereinto.

25. A method for handling dental elastic members attached to an elongated runner with a dispenser having a channel passing therethrough from at least one open end thereof and a slot extending outward from said opening and through along the tubing member from said at least one open end thereof, said method comprising:

slidably inserting said runner into and advancing said runner within said channel of said dispenser with said dental elastic members projecting outwardly from the dispenser through the slot thereof;

grasping one of said dental elastic members;

disengaging said selected dental elastic member from said runner; and installing said selected dental elastic member within a patient's mouth.

26. The method as claimed in claim 25, wherein said grasping step is accomplished with a placement tool.

27. The method as claimed in claim 25, wherein:

said slot is provided with a cutting edge;

said dental elastic members are interconnected to said elongated runner via a corresponding connector; and said disengaging step comprises contacting said corresponding connector with said cutting edge of the slot.

28. The method as claimed in claim 25, wherein said disengaging step comprises pulling said selected dental elastic member.

29. The method as claimed in claim 28, wherein:

said slot is provided with a cutting edge;

said dental elastic members are interconnected to said elongated runner via a corresponding connector; and said disengaging step further comprises contacting said corresponding connector with said cutting edge of the slot while pulling said selected dental elastic member.

* * * * *